United States Patent [19]

Hamaguchi et al.

[11] Patent Number: 5,019,394
[45] Date of Patent: May 28, 1991

[54] LIPOSOME COMPOSITION AND ITS PRODUCTION

[75] Inventors: Naoru Hamaguchi, Ibaraki; Katsumi Iga, Suita; Yasuaki Ogawa, Otokuni, all of Japan

[73] Assignee: Takeda Chemical Industries, Ltd., Osaka, Japan

[21] Appl. No.: 159,945

[22] Filed: Feb. 24, 1988

[30] Foreign Application Priority Data

Feb. 25, 1987 [JP] Japan .................................. 62-43442

[51] Int. Cl.[5] ...................... A61K 9/127; B01J 13/02; B01J 13/12; A61N 2/00
[52] U.S. Cl. .................................. 424/423; 264/4.1; 264/4.6; 424/450; 428/402.2; 600/10; 514/885
[58] Field of Search ...................... 264/4.1; 428/402.2; 424/450, 423

[56] References Cited

U.S. PATENT DOCUMENTS

| | | | |
|---|---|---|---|
| 4,217,344 | 8/1980 | Vanlerberghe et al. | 264/4.1 |
| 4,235,871 | 11/1980 | Papahadjopoulos et al. | 424/450 |
| 4,610,868 | 9/1986 | Fountain et al. | 264/4.1 |
| 4,670,185 | 6/1987 | Fujiwara et al. | 264/4.1 |
| 4,731,210 | 3/1988 | Weder et al. | 264/4.1 |
| 4,743,449 | 5/1988 | Yoshida et al. | 264/4.1 |
| 4,837,028 | 6/1989 | Allen | 424/450 |

FOREIGN PATENT DOCUMENTS

| | | |
|---|---|---|
| 17402 | 2/1984 | Australia . |
| 140085 | 9/1984 | European Pat. Off. . |
| 102324 | 10/1984 | European Pat. Off. . |
| 213523 | 11/1987 | European Pat. Off. . |
| 136508 | 7/1985 | Japan .................................. 424/450 |
| WO87/02364 | 4/1987 | PCT Int'l Appl. ................. 556/137 |
| 2151203 | 1/1987 | United Kingdom . |

OTHER PUBLICATIONS

Chem. Abstr., vol. 111, No. 17, Abst. 154375y, Zappia et al., PCT Int'l Appln. WO89/3389, Apr. 1989.
Bassett et al., "Use of Temperature-Sensitive Liposomes . . . ", *J. Urology*, vol. 135 (Mar. 1986), pp. 612–615.
Weinstein, J. N. in *Liposomes, From Biophysics to Therapeutics*, Ostro, M. J., ed. (1987), Marcel Dekker, pp. 280–285.
Derwent Abstract 85-213738/35, of JP 247834 (1985).

*Primary Examiner*—Richard D. Lovering
*Assistant Examiner*—John M. Covert
*Attorney, Agent, or Firm*—Wenderoth, Lind & Ponack

[57] ABSTRACT

The liposome compositions entrapping a drug are prepared by constituting the liposomal membrane with saturated phospholipids and anionic surfactants of high Krafft point at concentrations above their critical micelle concentrations. Thus obtained compositions circulate stably in blood for a long time after intravenous administration.

9 Claims, 1 Drawing Sheet

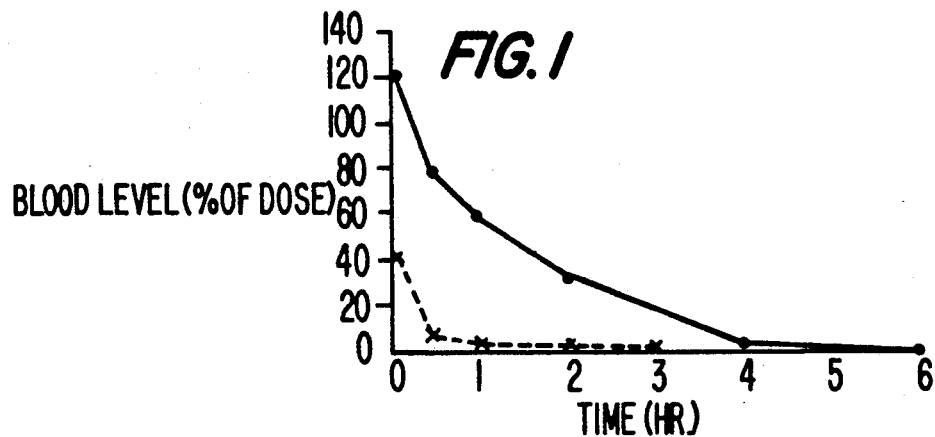
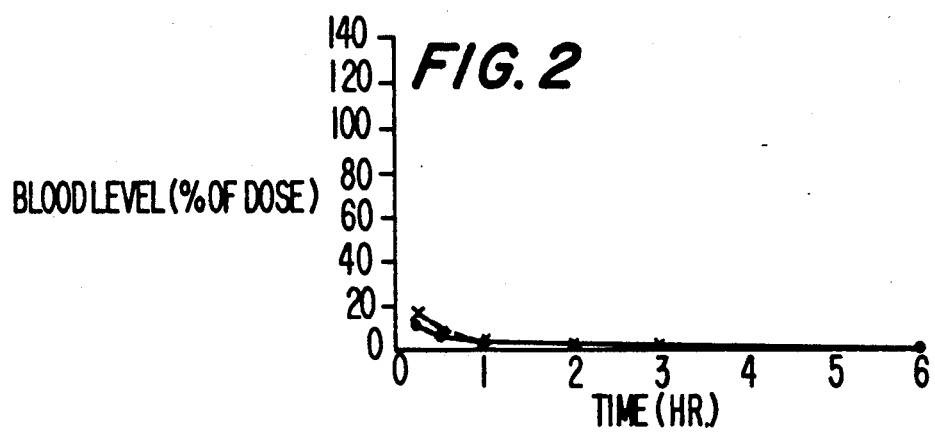
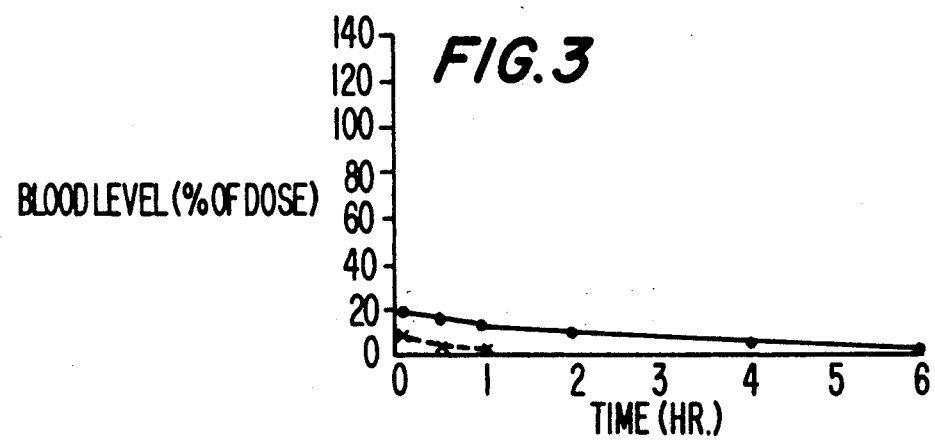
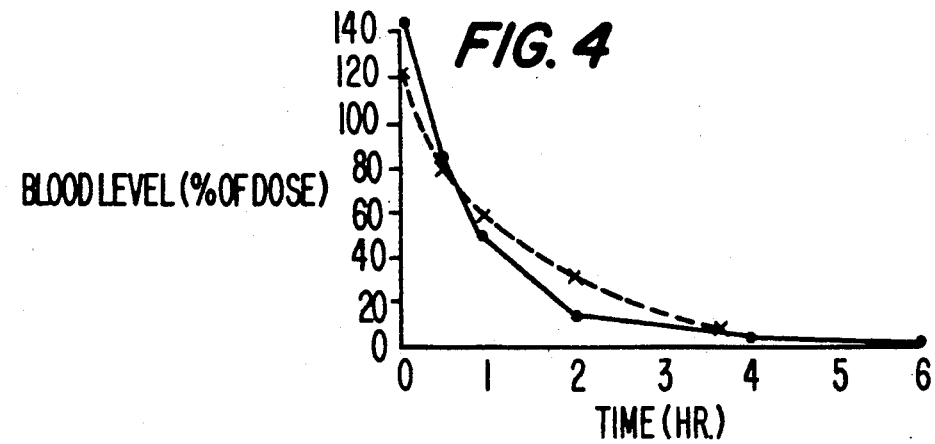

LIPOSOME COMPOSITION AND ITS PRODUCTION

This invention relates to liposome compositions and the method for their production.

The idea of Drug Delivery System (DDS) that a drug is targeted to a specified site by intravenous injection of a liposome preparation entrapping the drug has already been generalized [G. Gregoriadis et al., Receptor-mediated targeting of drugs, Plenum Press, New York, p 243-266(1980)]. The characteristic required primarily for such a liposome preparation in DDS is that liposome injected intravenously is stable for prolonged time in blood. However, liposome in itself is not very stable in blood because of interaction between the lipid, a component of the membrane, and the components in blood such as lipoprotein. In addition, liposome injected intravenously is recognized as a foreign substance by the reticulo-endothelial system (RES) on the basis of its physical properties and biochemical characteristics, so that it is apt to be eliminated from blood. Thus, liposome entrapping a drug injected intravenously is eliminated from blood rapidly, contrary to expectation. Therefore, it has been an important subject how to stabilize liposome in blood and avoid the recognition by RES so as to prolong the clearance in blood. For example, there is a report that the stability of liposome in blood increases by addition of cholesterol as a component of the liposomal membrane [C. G. Knight, "Liposomes; from physical structure to therapeutic applications", Elsevier, North Holland p 310-311(1981)]. However, it may be said that the effect of the addition depends greatly on the original composition of the liposomal membrane [Biochemica et Biophysica Acta, 839, 1-8(1985)]. There is also another report that delivery to RES can be controlled by coating the surface of the liposomal membrane with a glycoprotein containing sial groups as a component of the liposomal membrane [Chem. Pharm. Bull., 34, 2979-1988 (1986)]. There is a report to the contrary that such a glycoprotein containing sialic acid is delivered much to the liver, an organ of RES [Biochemica et Biophysica Acta, 497, 760-765 (1977)].

On the other hand, there is very little reported that a surfactant was used as a component of the liposomal membrane. The reason is that surfactants are generally considered to destabilize the structure of the liposomal membrane [Cell Technology (Saibo Kougaku), 2, 1136 (1983)], and rather frequently used to break the membrane [Biochemica et Biophysica Acta, 551, 295 (1979)]. Probably the only known method for preparation of liposome using a surfactant is that a homogeneous mixture of an ionic surfactant and a lipid is suspended in an aqueous phase at a concentration below the critical micelle concentration of the surfactant in the aqueous phase, to give a unilamellar liposome [the gazette of Japanese Unexamined Patent Publication No.89633/1984]. Liposome preparations obtained according to this method are, when given intravenously, rapidly eliminated from blood, and the purpose of DDS is not always fulfilled satisfactorily.

As described above, although the idea that liposome entrapping a drug is utilized for DDS by intravenous injection has been known, the liposome preparations produced by the conventional methods are rapidly eliminated from blood after intravenous injection; practically effective means to attain the purpose of DDS have not been developed yet.

Under these circumstances, the inventors investigated various methods to circulate liposome compositions stably for a prolonged time in blood. As a result the inventors found that the liposome compositions prepared by constituting the liposomal membrane with phospholipids containing saturated acyl groups in the presence of certain surfactants, i.e. anionic surfactants of Krafft point of 37° C. or more, are stable in blood, and have completed this invention after further research.

Namely this invention relates to (1) liposome compositions produced by entrapping a drug in liposome having a membrane constituted by a phospholipid having saturated acyl groups and an anionic surfactant of Krafft point of 37° C. or more, and (2) the method for production of liposome compositions entrapping a drug characterized in that membrane of said liposome is constituted by using an emulsion or a suspension prepared with a phospholipid having saturated acyl groups and an aqueous medium of an anionic surfactant of Krafft point of 37° C. or more at the concentration above the critical micelle concentration.

The phospholipids of which acyl groups are saturated acyl groups used for production of the liposome compositions of this invention (sometimes abbreviated simply as phospholipids hereinafter) include glycerophospholipids and sphingophospholipids of which acyl groups are saturated acyl groups. Such phospholipids include those of which two acyl groups are saturated alkyl groups having 8 or more carbon atoms each, at least one of which is a saturated alkyl group having 10 or more, preferably 12-18 carbon atoms. More desirably are used those of which both saturated acyl groups are saturated alkyl groups having 12-18 carbon atoms each. Such phospholipids include hydrogenated lecithin obtained by hydrogenation of lecithin of animal and plant origin (e.g. egg-yolk lecithin, soybean lecithin), and semisynthetic phospholipids obtained by combination of lauroyl, myristoyl, palmitoyl, stearoyl, etc. such as phosphatidyl ethanolamine, phosphatidyl serine, phosphatidyl glycerine, phosphatidyl inositol, and sphingomyelin. In more detail, those of which phase transition temperature is usually in the range of about 20°-80° C. are used preferably. For example those of which observed phase transition temperature is shown in the parentheses described below are used, such as dimyristoylphosphatidyl choline (DMPC 23.9° C.), palmitoylmyristoylphosphatidyl choline (PMPC, 27.2° C.), myristoylpalmitoylphosphatidyl choline (MPPC, 35.3° C.), dipalmitoylphosphatidyl choline (DPPC, 41.4° C.), stearoylpalmitoylphosphatidyl choline (SPPC, 44.0° C.), palmitoylstearoylphosphatidyl choline (PSPC, 47.4° C.), distearoylphosphatidyl choline (DSPC, 54.9° C.), dimyristoylphosphatidyl ethanolamine (DMPE, 50° C.), dipalmitoylphosphatidyl ethanolamine (DPPE, 60° C.), distearoylphosphatidyl ethanolamine (DSPE, above 60° C.), dimyristoylphosphatidyl serine (DMPS, 38° C.), dipalmitoylphosphatidyl serine (DPPS, 51° C.), distearoylphosphatidyl serine (DSPS, 50° C. or more), dimyristoylphosphatidyl glycerine (DMPG, 23° C.), dipalmitoylphosphatidyl glycerine (DPPG, 41° C.), distearoylphosphatidyl glycerine (DSPG, 55° C.), dipalmitoyl sphingomyelin (DPSM, 41° C.), and distearoyl sphingomyelin (DSSM, 57° C.).

As the anionic surfactants of Krafft point of 37° C. or more used in this invention (sometimes abbreviated simply as anionic surfactants hereinafter) those having sulfate group or sulfonate group are advantageously used. The surfactants of Krafft point of 37° C to 90° C are more preferably used in this invention. Such anionic surfactants include those represented by the following general formula:

wherein, R is an alkyl group having 12 or more carbon atoms which may be substituted with a sulfate group; X is —CONH—, —COO—,

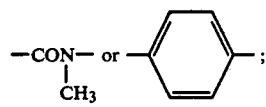

$Y_1$ is —CH$_2$CH$_2$—,

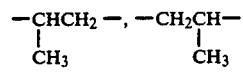

or —CH$_2$CH$_2$CH$_2$—;
$Y_2$ is —OCH$_2$CH$_2$—,

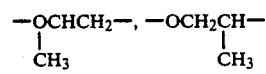

or —OCH$_2$CH$_2$CH$_2$—;
Z is —SO$_3$—M+, or —SO$_4$—M+, (M is an alkali metal element); m is 0 (direct bond) or 1; and n is an integer from 0 (direct bond) to 2, provided that when X is —CONH— or

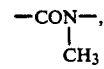

there is no $Y_2$ group, and when X is

n is 0 (direct bond).

The alkyl group represented by R usually has 12 to 25 carbon atoms, and those substituted with sulfate group are preferably those having 16 to 25 carbon atoms each, in which the sulfate group may be paired with an alkali metal ion (sodium, potassium, lithium) as the couple ion.

The following are examples of the anionic surfactants.

Anionic surfactants having sulfate group include salts of alkyl sulfate esters such as sodium hexadecyl sulfate (Krafft point; 43° C.) and sodium octadecyl sulfate (Krafft point; 58° C.); salts of alkyl disulfate esters such as sodium hexadecyl disulfate ester (Krafft point; 39° C.) and sodium octadecyl disulfate ester (Krafft point; 45° C.); salts of alkylether sulfate esters such as sodium octadecylether sulfate ester (Krafft point; 46° C.) and sodium octadecyl diether sulfate ester (Krafft point; 40° C.); and salts of fatty acid alkanolamide sulfate esters such as sodium palmitoyl ethanolamide sulfate ester (Krafft point; 42° C.), sodium stearoyl ethanolamide sulfate ester (Krafft point; 53° C.), sodium palmitoyl propanolamide sulfate ester (Krafft point;47° C.), and sodium stearoyl propanolamide sulfate ester (Krafft point; 57° C.). Anionic surfactants having sulfonate group include salts of alkanesulfonic acids such as sodium dodecanesulfonate (Krafft point; 38° C.), sodium tetradecanesulfonate (Krafft point;48° C.), sodium pentadecanesulfonate (Krafft point; 48° C.), sodium hexadecanesulfonate (Krafft point; 57° C.), sodium heptadecanesulfonate (Krafft point; 62° C.), and sodium octadecanesulfonate (Krafft point; 70° C.); salts of alkylbenzenesulfonates such as sodium dodecylbenzenesulfonate (Krafft point; 40° C.), sodium tetradecylbenzenesulfonate (Krafft point; 43° C.), sodium hexadecylbenzenesulfonate (Krafft point; 46° C.), and sodium octadecylbenzenesulfonate (Krafft point; 56° C.); salts of acyloxyethanesulfonic acids such as sodium myristoyloxyethanesulfonate (Krafft point; 39° C.), sodium palmitoyloxyethanesulfonate (Krafft point; 51° C.), and sodium stearoyloxyethanesulfonate (Krafft point; 51° C.); and salts of acyltaurines such as sodium palmitoyltaurine (Krafft point; 43° C.), sodium stearoyltaurine (Krafft point; 58° C.), sodium palmitoylmethyltaurine (Krafft point; 43° C), and sodium stearoylmethyltaurine (Krafft point; 58° C). Among these anionic surfactants, salts of acyltaurines or acylmethyl taurines are particularly preferably used because of the high stability in blood of the liposome preparations and their industrial supply.

In the following, the method for production of the liposome compositions of this invention is described.

The liposome compositions of this invention are prepared so that the phase transition temperature may generally be in the range of about 37 to 60° C., preferably about 40° to 55° C. Adjustment of the phase transition temperature can be achieved by adequate selection of the kind and the combination ratio of phospholipids and anionic surfactants used. The phase transition temperature of the liposomal membrane thus combined can be confirmed by calorimetry such as DSC (Differential Scanning Calorimeter) or by measurement of the amount released of the drug entrapped in liposome. To adjust the phase transition temperature of the liposomal membrane in the range described above, about 0.5-50 weight parts, preferably about 5-20 weight parts of an anionic surfactant is used per 100 weight parts of a phospholipid. By adjusting the phase transition temperature of the liposomal membrane in the range described above, the purpose of this invention that the clearance in blood of the liposome compositions obtained is prolonged can be attained advantageously.

For producing the liposome preparations of this invention, aqueous mediums containing anionic surfactants at the concentrations above their critical micelle concentrations are used. The critical micelle concentrations can be determined by usual methods, for example by investigating the relation between physical properties such as surface tension, osmotic pressure coefficient, and electric conductivity, and the concentration of the anionic surfactant [Masayuki Nakagaki and Naofumi Koga, "Drug Physicochemistry (Yakuhin Butsurikagaku)", 3rd Edn., p 111 (1969), Nankodo]. Therefore, aqueous mediums can be prepared by using these measurements as indices so that the concentration of the anionic surfactant may be above the critical micelle concentration and the ratio of the amount of the anionic surfactant to that of the phospholipid may be in the range described above. These aqueous mediums may be prepared by dissolving an anionic surfactant in an aqueous medium at a temperature higher than the Krafft point, or by suspending at a temperature lower than the Krafft point. It is desirable that a water-soluble drug is dissolved in these aqueous solutions, and, if necessary, other additives (e.g. sugars and salts as osmotic pressure modifiers, buffers as pH modifiers) may be dissolved. The content of a drug depends on the purpose of the therapy and the potency of the drug.

From the aqueous mediums thus obtained and phospholipids, emulsions or suspensions are prepared to constitute liposome according to the per se known methods for preparations of REV, MLV, SUV and other liposome preparations. For example, liposome compositions from emulsions are prepared as follows; first a phospholipid is dissolved in an organic solvent (e.g. diethylether, isopropylether, chloroform, which are used separately or in combination), to which the aqueous medium of an anionic surfactant described above is added, and a w/o type emulsion is prepared by a conventional method. From this w/o type emulsion, a liposome composition is prepared according to the method described in Proc. Natl. Acad. Sci. USA, 75, 4194 (1978), or the method described in the gazette of Japanese Unexamined Patent Publication No.118415/1980. The amount of an organic solvent used for preparation of emulsion is generally 2–10 times the amount of the aqueous medium to be entrapped in liposome. The amount of phospholipid is about 10–100 μmol per 1 ml of the liquid to be included, and it is generally desirable that the phospholipid is dissolved in the organic solvent beforehand.

For emulsification to obtain a w/o type emulsion, the conventional methods are applicable such as stirring, pressurization, and sonication. Homogenous emulsions can be obtained by sonication for about 1 to 20 minutes with a 20 KHz probe type sonicator. In the method of this invention using an anionic surfactant, emulsification is easy and a homogenous fine emulsion can be obtained.

From these w/o type emulsions thus obtained, the solvent is removed according to the conventional methods. For example, the solvent can be evaporated off with a rotary evaporator. Evaporation is performed desirably at a temperature of 40° C. or more, under reduced pressure of about 60–400 mmHg in the initial stage and about 100–700 mmHg after the content has formed a gel. Further evaporation to remove the solvent will give a REV (reverse-phase evaporation vesicle) liposome preparation. This liposome constitutes unilamellar or oligolamellar (having about 10 or less layers of which each layer is consisted of a dual lipid membrane) entrapping a drug.

On the other hand, liposome preparations of multilamellar vesicles (MLV) type can be obtained by evaporating the organic solvent from the solution of a phospholipid in an organic solvent prepared similarly as described above under reduced pressure to form a thin film of the phospholipid, followed by adding an aqueous medium of an anionic surfactant containing a drug and allowing the aqueous medium to disperse at 40° C or more. The MLV preparation thus obtained can be shaken with a probe type sonicator to give a liposome preparation of small unilamellar vesicle (SUV) type.

The method for production of liposome compositions of this invention is applicable also to stable plurilamellar vesicle (SPLV) method (the gazette of Japanese Unexamined Patent Publication No.500952/1984) and the dehydration-rehydration vesicle method [C. Kirby et al., Biotechnology, Nov., 979 (1984)]. In the case of a drug that is fat soluble but slightly soluble in water, a liposome composition can be obtained by entrapping the drug which has been dissolved in the solution of a lipid in an organic solvent as described above. Such a liposome preparation may be used as it is, or, if necessary, after preparations of particles of desirable size by, for example, nuclepore filter or gel filtration. It is desirable to eliminate the free unentrapped drug prior to use by, for example, centrifugation, gel filtration, or dialysis.

The drugs used in this invention are not particularly defined as far as they are used for DDS, including antitumor agents such as platinum compounds (e.g. cisplatin, carboplatin, spiroplatin), adriamycin, mitomycin C, actinomycin, ansamitocin, bleomycin, 5-FU, and methotrexate; lymphokins such as natural and gene recombinant interferons ($\alpha$, $\beta$, $\gamma$), and natural and gene recombinant interleukins; physiologically active peptides such as manganese superoxide desmutase (SOD) and its derivative superoxide desmutase PEG (PEG-500) (the gazette of Japanese Unexamined Patent Publication No.16685/1983 and EPC Patent Application Laid-Open No. 0210761); antibiotics, for example beta lactam antibiotics such as sulfazecin, and amino glycoside antibiotics such as gentamycin, streptomycin, and kanamycin; vitamins such as cyanocobalamin and ubiquinone; antiprotozoal agents such as meglumine antimonate; enzymes such as alkali phosphatase; anticoagulants such as heparin; antiallergic agents such as amlexanox; immunoactivating agents such as muramyl dipeptide, muramyl tripeptide, and TMD-66 [Cancer (Gann 74 (2), 192–195 (1983)]; agents for circulatory system such as propranolol; and metabolism activating agents such as glutathione. This invention is preferably applicable particularly to the water soluble drugs because of the purpose of the invention. Such drugs include those of which logarithm of the partition coefficient between octanol and water is 10 or less. The drug is used in an amount which is effective to achieve the objective of administering the drug.

The liposome compositions of this invention are used by intravenous administration by injection or by drip infusion of a suspension of an appropriate amount of a solution or emulsion in for example physiological saline according to the purpose of the therapy.

The liposome compositions of this invention are characterized by the use of saturated phospholipids and anionic surfactants of high Krafft point at concentrations above their critical micelle concentrations.

The liposome compositions of this invention circulate through the body stably in blood for a long time after intravenous administration, which is useful to reduce the toxicity of the drug, enhance the targeting effect of the drug to a specified tissue, and increase the persisting therapeutical effect of the drug. Particularly the liposome compositions of this invention including antitumor agents are expected to enhance the therapeutic effect when administered during hyperthermia; for this purpose, liposome preparations of which phase transition temperature of the liposomal membrane is in the range of about 40°–55° C. are preferably used.

BRIEF DESCRIPTION OF THE DRAWINGS

FIGS. 1, 2 and 3 show the relation between the time after intravenous administration of the liposome composition entrapping 6-CF in rat in Experimental Example 1-2 and the 6-CF blood level. FIG. 4 shows the relation between the time after intravenous administration of the liposome composition entrapping 6-CF or CDDP in rat in Experimental Example 2—2 and the blood level. The blood level is shown as % of dose on the assumption that blood volume is 10% of body weight.

EXAMPLES

In the following this invention is illustrated in the concrete in Examples, Test examples, and Experimental Examples.

Example 1

270 mg of DPPC and 30 mg of DSPC were dissolved in 70 ml of 1:1 mixture of chloroform and isopropylether in a 1—1 beaker. To 10 ml of an aqueous solution of 6-carboxyfluorescein (6-CF), pH 7, which had been prepared beforehand so that the osmotic pressure might be the same as that of the physiological saline, 30 mg of sodium stearoylmethyltaurine (SMT) was added at room temperature. SMT remained almost insoluble, but was dissolved rapidly by forming micelles at a temperature above the Krafft point. Then this solution was added to the solution of the phospholipid in an organic solvent, and emulsified by a probe type sonicator (Ohtake, Japan), to give a w/o type emulsion. Sonication at 50 watt for 30 seconds was repeated 10 times. This emulsion was charged to a rotary evaporator to evaporate off the organic solvent at 60° C. under reduced pressure, to give REV. The pressure in the evaporator was reduced greatly in the initial stage, but then adjusted in the course of evaporation of the organic solvent to prevent bumping. A small amount of the organic solvent remained in REV was further evaporated off by blowing nitrogen gas. Then an appropriate amount of physiological saline was added to REV to make 10 ml, filtered through a 1.2 micron filter (Acrodisc, Gelman), and dialyzed through a dialysis membrane (Spectrapor, Spectrum Medical) against physiological saline for 24 hours, to give a liposome compostition entrapping 6-CF. The entrapment ratio of 6CF in this liposome composition was 33.2% as determined by quantification of 6-Cf entrapped in liposome (Note 1).

(Note 1) Quantification of 6-CF in liposome and calculation of entrapment ratio 0.1 ml of a liposome composition is diluted 100 times with phosphate bufferized physiological saline (PBS, pH 7.2), then further diluted 100 times with 0.02% Triton X-100-containing PBS, heated at 60° C. for 30 minutes to break liposome; total 6-CF amount in the lipoxome suspension was determined by measurement of the intensity of fluorescence of the solution (Hitachi, F3000 Fluorospectrometer, excitation wave length 494 nm, measurement wave length 515 nm). Separately 0.1 ml of the liposome composition is diluted 10000 times with PBS, 2.5 ml of which was filtered through a centrifugal filter (Centrisart, SM13249E, Sartorius), and the amount of free unentrapped 6-CF in the liposome suspension was determined by measurement of the intensity of fluorescence of the filtrate.

entrapment ratio=[(total amount of 6-CF in liposome composition)−(amount of free 6-CF in liposome composition)]/(amount of 6-CF used for preparation of liposome composition)×100

Example 2

15 mg of SMT was used in place of 30 mg of SMT in Example 1 and treated similarly as in Example 1, to give a liposome composition of the 6-CF entrapment ratio of 34.9%.

Example 3

45 mg of SMT was used in place of 30 mg of SMT in Example 1 and treated similarly as in Example 1, to give a liposome composition of the 6-CF entrapment ratio of 39.4%.

Example 4

60 mg of SMT was used in place of 30 mg of SMT in Example 1 and treated similarly as in Example 1, to give a liposome composition of the 6-CF entrapment ratio of 46.3%.

Example 5

30 mg of sodium palmitoylmethyltaurine (PMT) was used in place of 30 mg of SMT in Example 1 and treated similarly as in Example 1, to give a liposome composition of the 6-CF entrapment ratio of 32.3%

Example 6

30 mg of sodium octadecanesulfonate (ODS) was used in place of 30 mg of SMT in Example 1 and treated similarly as in Example 1, to give a liposome composition of the 6CF entrapment ratio of 33.3%.

Example 7

15 mg of ODS was used in place of 30 mg of ODS in Example 1 and treated similarly as in Example 1, to give a liposome composition of the 6-CF entrapment ratio of 24.1%.

Example 8

45 mg of ODS was used in place of 30 mg of ODS in Example 1 and treated similarly as in Example 1, to give a liposome composition of the 6-CF entrapment ratio of 38.3%.

Example 9

60 mg of ODS was used in place of 30 mg of ODS in Example 1 and treated similarly as in Example 1, to give a liposome composition of the 6-CF entrapment ratio of 40.1%.

Example 10

210 mg of DPPC and 90 mg of DSPC were used in place of 270 mg of DPPC and 30 mg of DSPC in Example 1 and treated similarly as in Example 1, to give a liposome composition of the 6-CF entrapment ratio of 24.1%.

Example 11

300 mg of DPPC was used in place of 270 mg of DPPC and 30 mg of DSPC in Example 1 and treated similarly as in Example 1, to give a liposome composition of the 6-CF entrapment ratio of 35.2%.

Example 12

210 mg of DPPC and 90 mg of DSPC were used in place of 270 mg of DPPC and 30 mg of DSPC in Example 1 and treated similarly as in Example 1, to give a liposome composition of the 6-CF entrapment ratio of 28.3%.

Example 13

300 mg of DPPC was used in place of 270 mg of DPPC and 30 mg of DSPC in Example 6 and treated similarly as in Example 1, to give a liposome composition of entrapment ratio of 34.6%.

Example 14

30 mg of sodium palmitoyltaurine (PT) was used in place of 30 mg of SMT in Example 1 and treated similarly as in Example 1, to give a liposome composition of the 6-CF entrapment ratio of 22.4%.

Example 15

360 mg of DPPC and 40 mg of DSPC were dissolved in 40 ml of chloroform in a 1-l beaker. The organic solvent was evaporated off in a rotary evaporator and a lipidic film formed on the glass wall. A trace of the organic solvent remaining in the film was removed by blowing nitrogen gas. To the film thus prepared 10 ml of 6-CF solution containing 40 mg of SMT used in Example 1, which had been kept at 60° C., was added at 60° C., and allowed to disperse by vortex, to give a MLV liposome. The MLV preparation thus obtained was treated by sonication at 50 watt for about 10 minutes with the probe type sonicator used in Example 1, to give a SUV. Similarly as in Example 1, the preparation was further subjected to filtration and dialysis, to give a liposome composition of 6-CF entrapment ratio of 5.7%.

Example 16

280 mg of DPPC and 120 mg of DSPC were used in place of 360 mg of DPPC and 40 mg of DSPC in Example 15 and treated similarly as in Example 15, to give a liposome composition of the 6-CF entrapment ratio of 6.3%

Example 17

400 mg of DPPC was used in place of 360 mg of DPPC and 40 mg of DSPC in Example 15 and treated similarly as in Example 15, to give a liposome composition of the 6-CF entrapment ratio of 6.0%.

Example 18

40 mg of PMT was used in place of 40 mg of SMT in Example 15 and treated similarly as in Example 15, to give a liposome composition of the 6-CF entrapment ratio of 6.8%.

Example 19

40 mg of ODS was used in place of 40 mg of SMT in Example 15 and treated similarly as in Example 15, to give a liposome composition of the 6-CF entrapment ratio of 6.5%.

Example 20

40 mg of sodium palmitoyltaurine (PT) was used in place of 40 mg of SMT in Example 15 and treated similarly as in Example 15, to give a liposome composition of the 6-Cf entrapment ratio of 6.0%.

Experimental Example 1—1

Control liposome compositions were prepared which did not contain anionic surfactants and corresponded respectively to the liposome compositions obtained in Examples 1, 10, 11, 15, 16 and 17 described above. Another control liposome composition was prepared in a similar manner as in Example 1 by using 200 mg of egg-yolk phosphatidyl choline containing unsaturated acyl groups, 100 mg of cholesterol, and 30 mg of SMT in place of 270 mg of DPPC, 30 mg of DSPC, and 30 mg of SMT used in Example 1. A SMT-free control liposome composition corresponding to this preparation was prepared. Another control liposome composition was prepared by using sodium dodecyl sulfate (SDS, Krafft point; 9° C.) in place of SMT used in Example 15.

Experimental Example 1-2

The liposome composition obtained in Example 1 described above, and the liposome composition prepared similarly but without the anionic surfactant, 0.1-0.5 ml each, were given intravenously in rat, and elimination from blood was investigated (Note 2); the results are shown in FIG. 1. As shown in FIG. 1, the blood levels of the liposome containing the anionic surfactant (—•—) were much higher than those of the control liposome without the surfactant (- - - x - - -). The liposome compositions obtained in Examples 1, 6, 10, 15, 18, 19 and 20, 0.1-0.5 ml each, were given intravenously in rat, and the amount of liposome remaining in blood one hour after administration was 9.7, 11.9, 26.4, 2.7, 2.3, 2.8, and 2.2 times as much as that of the respective control liposome prepared similarly but without the anionic surfactant. On the other hand, as shown in FIG. 2, the anionic surfactant-containing liposome prepared from egg-yolk phosphatidyl choline and cholesterol (—•—) was eliminated from blood as rapidly as the control liposome (- - - x - - -). FIG. 3 shows the elimination from blood after intravenous administration in rat of 0.2 ml either of the SDS-containing liposome obtained in Experimental Example 1—1 described above (- - - x - - -) or of the liposome prepared similarly but without SDS (—•—). The results shown in these FIGS. clearly indicate that the liposome compositions of this invention prepared by using a phospholipid containing saturated acyl groups and an anionic surfactant of Krafft point of 37° C. or more as the components of the liposomal membrane are characterized by the much prolonged elimination time from blood after intravenous administration as compared with the control liposome compositions.

Experimental 1-3

The liposome compositions obtained in Examples 1, 15, 18, and 19, and Experimental Example 1—1 described above were given intravenously in rat, and the level of 6-CF in liver was determined to know the delivery of liposome to RES (Note 2); the results are shown in Table 1. These results indicate that the elimination time of liposome from blood was prolonged and delivery to RES such as the liver was reduced.

TABLE 1

| liposome preparation | Liposome level in liver one hour after administration (%) | |
|---|---|---|
| | with anionic surfactant | without anionic surfactant |
| Example 1 | 16.7 | 30.1 |
| Example 15 | 16.9 | 44.7 |
| Example 18 | 19.1 | 44.7 |
| Example 19 | 15.0 | 44.7 |

(Note 2) Measurement of 6-CF liposome level in blood and in liver

To 0.2 ml of heparinized blood drawn from the caudal vein, 10 ml of PBS was added to give a blood suspension. This suspension was centrifuged (3000 rpm, 10 minutes), and to 5 ml of the resultant supernatant 0.05 ml of Triton X-100 was added and heated at 60°-70° C. to break liposome; the liposome level in blood was determined by measurement of fluorescence of 6-CF released. The liver extirpated after abdominal section and exsanguination was immersed in PBS containing 0.02 % Triton X-100 to make 100 ml. The tissue was homogenized by a homogenizer (Polytron, Kinematica), and heated at 60°-70° C., to give a homogenate in which all of the 6-CF had been released. The homogenate was subjected to ultracentrifugation (50000g, 10 minutes), diluted 20–50 times, and filtrated through a 0.45 micron membrane filter (Acrodisk, Gelman); the liposome level in liver was determined by measurement of the fluorescence of the filtrate.

Experimental Example 1-4

Heat release from 10000 times dilutions with PBS (2% plasma) of the liposome compositions obtained in Examples 1, 2, and 6, and the respective control preparations containing no anionic surfactants was investigated by continuous measurement of the amount of 6-CF released from liposome with a fluorometer connected to a programmed temperature system, to follow the phase transition of liposomal membrane (change from gel to liquid crystal). The initiation temperature of heat release and the phase transition temperature determined from the heat release curve are shown in Table 2. The phase transition temperature was measured with a thermal analyzing system (SEIKO I & E, SSC 50000 type, 2° C./min). Both temperatures are closely related to each other.

TABLE 2

Phase transition temperature (°C.) of liposomal membrane and heat release initiation temperature (°C.) of 6-CF from liposome

| liposome composition | phase transition temperature | heat release initiation temperature |
| --- | --- | --- |
| Example 1 | 42.3 | 36.1 |
| Example 6 | 43.7 | 39.3 |
| Example 10 | 42.8 | 36.3 |
| without surfactant | 41.9 | 37.9 |

Example 21

A 500 μg/ml solution of cisplatin (CDDP) in physiological saline was used in place of the 6-CF solution obtained in Example 1 and treated similarly as in Example 1, to give a liposome composition of the CDDP entrapment ratio of 23.5% and the phase transition temperature of 42.7° C.

(Note 3) Measurement of CDDP content in liposome 0.1 ml of a liposome composition was suspended in 5 ml of physiological saline, and 2.5 ml of the suspension was freeze-dried and heated; the resultant solution containing broken liposome, about 2.5 ml, was filtrated through Centrisalt, and to 0.1 ml of the filtrate 2 ml of 0.1 N NaOH solution containing 10% of diethyldithiocarbamate (DDTC) was added and kept at room temperature for 30 minutes; the resultant adduct was extracted with 5 ml of n-hexane and the extract was analyzed by HPLC (column; Zorbax CN, solution; n-hexane/isopropylalcohol =8/2; UV=250 nm) to determine the total CDDP amount in the liposome suspension. Separately the remaining solution of liposome in physiological saline, about 2.5 ml, was filtrated through Centrisalt and the amount of free CDDP remaining unentrapped in liposome was determined under the same conditions as described above.

Example 22

A 500 μg/ml solution of cisplation (CDDP) in physiological saline was used in place of the 6-CF solution used in Example 2 and treated similarly as in Example 2, to give a liposome composition of the CDDP entrapment ratio of 21.4%.

Example 23

A 500 μg/ml solution of cisplatin (CDDP) in physiological saline was used in place of the 6-CF solution used in Example 3 and treated similarly as in Example 3, to give a liposome composition of the CDDP entrapment ratio of 25.8%.

Example 24

A 500 μg/ml solution of cisplatin (CDDP) in physiological saline was used in place of the 6-CF solution used in Example 5 and treated similarly as in Example 5, to give a liposome composition of the CDDP entrapment ratio of 24.0%.

Example 25

A 500 μg/ml solution of cisplation CDDP) in physiological saline was used in place of the 6-CF solution used in Example 6 and treated similarly as in Example 6, to give a liposome composition of the CDDP entrapment ratio of 21.8% and the phase transition temperature of 43.9° C.

Example 26

A 500 μg/ml solution of cisplatin (CDDP) in physiological saline was used in place of the 6-CF solution used in Example 7 and treated similarly as in Example 7, to give a liposome composition of the CDDP entrapment ratio of 21.9%.

Example 27

A 500 μg/ml solution of cisplatin (CDDP) in physiological saline was used in place of the 6-CF solution used in Example 8 and treated similarly as in Example 8, to give a liposome composition of the CDDP entrapment ratio of 24.9%.

Example 28

A 500 μg/ml solution of cisplatin (CDDP) in physiological saline was used in place of the 6-CF solution used in Example 10 and treated similarly as in Example 10, to give a liposome composition of the CDDP entrapment ratio of 23.3%.

Example 29

A 500 μg/ml solution of cisplatin (CDDP) in physiological saline was used in place of the 6-CF solution used in Example 11 and treated similarly as in Example 11, to give a liposome composition of the CDDP entrapment ratio of 27.7% and the pahse transition temperature of 41.9° C.

Example 30

A 500 µg/ml solution of cisplatin (CDDP) in physiological saline was used in place of the 6-CF solution obtained in Example 12 and treated similarly as in Example 12, to give a liposome composition of the CDDP entrapment ratio of 24.0%.

Example 31

A 500 µg/ml solution of cisplatin (CDDP) in physiological saline was used in place of the 6-CF solution used in Example 13 and treated similarly as in Example 13, to give a liposome composition of the CDDP entrapment ratio of 24.5% and the phase transition temperature of 42.5° C.

Example 32

A 500 µg/ml solution of cisplatin (CDDP) in physiological saline was used in place of the 6-CF solution used in Example 14 and treated similarly as in Example 14, to give a liposome composition of the CDDP entrapment ratio of 25.0%.

Example 33

A 500 µg/ml solution of cisplatin (CDDP) in physiological saline was used in place of the 6-CF solution used in Example 15 and treated similarly as in Example 15, to give a liposome composition of the CDDP entrapment ratio of 4.8%.

Example 34

A 500 µg/ml solution of cisplatin (CDDP) in physiological saline was used in place of the 6-CF solution obtained in Example 16 and treated similarly as in Example 16, to give a liposome composition of the CDDP entrapment ratio of 5.0%.

Example 35

A 500 µg/ml solution of cisplatin (CDDP) in physiological saline was used in place of the 6-CF solution used in Example 17 and treated similarly as in Example 17, to give a liposome composition of the CDDP entrapment ratio of 5.2%.

Example 36

A 500 µg/ml solution of cisplatin (CDDP) in physiological saline was used in place of the 6-CF solution used in Example 18 and treated similarly as in Example 18, to give a liposome composition of the CDDP entrapment ratio of 4.3%.

Example 37

A 500 µg/ml solution of cisplatin (CDDP) in physiological saline was used in place of the 6-CF solution used in Example 19 and treated similarly as in Example 19, to give a liposome composition of the CDDP entrapment ratio of 4.9%.

Example 38

A 500 µg/ml solution of cisplatin (CDDP) in physiological saline was used in place of the 6-CF solution used in Example 20 and treated similarly as in Example 20, to give a liposome composition of the CDDP entrapment ratio of 4.7%.

Experimental Example 2-1

Liposome compositions containing no anionic surfactants were prepared as the respective control compositions of the liposome preparations obtained in Examples 21, 28, 29, 33, 34, and 35.

Experimental Example 2-2

The 6-CF level in blood until 6 hours after intravenous administration in rat of the liposome composition of Example 1 was compared with the CDDP level (Note 4) after intravenous administration of the liposome composition of Example 15 in rat, and the result is shown in FIG. 4. At any time point, the level of CDDP was simillar to that of 6-CF, suggesting that the CDDP liposome composition (—•—) may behave similarly to the 6-CF liposome composition (- - - x - - -). Also the liposome compositions obtained in Examples 21, 22, 25, 26, and 29 showed values as high as those obtained with the 6-CF liposome compositions These results also inidicate that the liposome compositions of this invention prepared by using a phospholipid containing saturated acyl groups and an anionic surfactant of Krafft point of 37° C. or more are characterized by the much prolonged elimination time from blood after intravenous administration, as compared with the control liposome compositions.

(Note 4) Measurement of CDDP level in blood

To 0.2 ml of heparinized blood obtained from caudal vein, 2 ml of PBS was added to give a blood suspension. To 1 ml of the supernatant obtained by centrifugation of the suspension, 1 ml of DDTC solution was added; the total amount of CDDP in blood was determined similarly to the method of measurement of CDDP amount described above.

Experimental Example 2-3

The SMT content of the composition in Example 21 described above was determined (Note 5), and the result showed that about 90% of the amount charged for preparation of the liposome composition remained. This value was much higher than the CDDP entrapment ratio of 23.5%, indicating that SMT certainly constitutes the liposomal membrane, and that about 150 molecules of SMT are present per 1000 molecules of the phospholipid in the liposomal membrane.

(Note 5) Measurement of SMT content 15 mg of methylene blue, 6 g of concentrated sulfuric acid, and 25 g of anhydrous sodium sulfate were dissolved in distilled water, to make 500 ml of a reaction test solution. To 5 ml of this reaction test solution, 10 ml of a diluted liposome composition (10000 times) and 5 ml of chloroform were added, and allowed to separate into two layers after thorough shaking; absorbance (653 nm) of the chloroform layer was measured. Absorbance of SMT solutions of various concentrations (less than 10 ppm) was measured to make a calibration curve. A blank test was conducted by using the SMT-free liposome composition in Experimental Example 2-1.

Example 39

A 308 µg protein/ml aqueous solution of interleukin 2 (IL-2) (in 25 mM ammonium acetate solution pH 6) was used in place of the 6-CF solution used in Example 11 and treated similarly as in Example 11, to give a liposome composition of this invention.

Example 40

A 308 µg protein/ml aqueous solution of IL-2 was used in place of the 6-CF solution used in Example 13 and treated similarly as in Example 13, to give a liposome composition of this invention.

Example 41

A 100 μg/ml aqueous solution of ansamitocin was used in place of the 6-CF solution used in Example 11 and treated similarly as in Example 11, to give a liposome composition of this invention entrapping ansamitocin.

Example 42

A 100 μg/ml aqueous solution of ansamitocin was used in place of the 6-CF solution used in Example 13 and treated similarly as in Example 13, to give a liposome composition of this invention entrapping ansamitocin.

Example 43

A 5 mg/ml solution of methotrexate in physiological saline was used in place of the 6-CF solution used in Example 11 and treated similarly as in Example 11, to give a liposome composition of this invention entrapping methotrexatae.

Example 44

A 5 mg/ml solution of methotrexate in physiological saline was used in place of the 6-CF solution used in Example 13 and treated similarly as in Example 13, to give a liposome composition of this invention entrapping methotrexate.

Example 45

A 200,μg/ml solution of mitomycin C in physiological saline was used in place of the 6-CF solution used in Example 11 and treated similarly as in Example 11, to give a liposome composition of this invention entrapping mitomycin C.

Example 46

A 200 /μg/ml solution of mitomycin C in physiological saline was used in place of the 6-CF solution used in Example 13 and treated similarly as in Example 13, to give a liposome composition of this invention entrapping mitomycin C.

Example 47

A 1 mg/ml solution of adriamycin in physiological saline was used in place of the 6-CF solution used in Example 11 and treated similarly as in Example 11, to give a liposome composition of this invention entrapping adriamycin.

Example 48

A 1 mg/ml solution of adriamycin in physiological saline was used in place of the 6-CF solution used in Example 13 and treated similarly as in Example 11, to give a liposome composition of this invention entrapping adriamycin.

Example 49

A 3 mg/ml solution of bleomycin in physiological saline was used in place of the 6-CF solution used in Example 11 and treated similarly as in Example 11, to give a liposome composition of this invention entrapping bleomycin.

Example 50

A 3 mg/ml solution of bleomycin in physiological saline was used in place of the 6-CF solution used in Example 13 and treated similarly as in Example 13, to give a liposome composition of this invention entrapping belimycin.

What is claimed is:

1. A liposome composition for intravenous administration of a therapeutic water-soluble drug, said composition comprising a plurality of liposomes containing the water-soluble drug, said liposomes having a membrane composed of a phospholipid of which acyl groups are saturated acyl groups and an anionic surfactant having a Krafft point of 37° C. or more, and said anionic surfactant being an alkali metal salt of acyltaurine or acylmethyltaurine.

2. The composition according to claim 1, wherein the phase transition temperature of the liposomal membrane is in the range of about 37° to 60° C.

3. The composition according to claim 1, wherein the water-soluble drug has a logarithm of partion coefficient between octanol and water of 10 or less.

4. The composition according to claim 1, wherein the water-soluble drugs are antitumor agents, lymphokines, physiologically active peptides, antibiotics, vitamins, antiprotozoal agents, enzymes, anticoagulants, antiallergic agents, immunoactivating agents, agents for circulatory system or metabolism activating agents.

5. The composition according to claim 4, wherein the antitumor agents are platinum compounds.

6. The composition according to claim 5, wherein the platinum compound is cisplatin.

7. The composition according to claim 4, wherein an antitumor agent is entrapped in the liposome of which membrane has a phase transition temperature of about 40° to 55° C.

8. A method of producing a liposome composition for intravenous administration of a therapeutic water-soluble drug, comprising
    (1) preparing an aqueous medium containing an anionic surfactant having a Krafft point of 37° C. or more at a concentration above the critical micelle concentration, said anionic surfactant being an alkali metal salt of acyltaurine or acylmethyltaurine,
    (2) mixing the resulting aqueous medium with a phospholipid of which acyl groups are saturated acyl groups so that the amount of the anionic surfactant is in the range of about 0.5 to 50 parts by weight per 100 parts by weight of the phospholipid, to obtain an emulsion or a suspension,
    wherein a therapeutically effective amount of the water-soluble drug is added during either steps (1) or (2) above, and
    (3) preparing liposomes from the resulting emulsion or suspension so that said liposomes have a membrane composed of said surfactant and said phospholipid.

9. The method according to claim 8, wherein the liposomes are prepared by a method of producing REV, MLV, SUV or SPLV.

* * * * *